(12) United States Patent
Seaver et al.

(10) Patent No.: US 10,244,954 B2
(45) Date of Patent: Apr. 2, 2019

(54) IMPLANTABLE BIO-PRESSURE TRANSPONDER

(71) Applicant: ARKIS BIOSCIENCES INC., Knoxville, TN (US)

(72) Inventors: Chad E. Seaver, Knoxville, TN (US); James A. Killeffer, Knoxville, TN (US); James C. Arnott, Knoxville, TN (US)

(73) Assignee: Arkis Biosciences Inc., Knoxville, TN (US)

( * ) Notice: Subject to any disclaimer, the term of this patent is extended or adjusted under 35 U.S.C. 154(b) by 906 days.

(21) Appl. No.: 14/525,270

(22) Filed: Oct. 28, 2014

(65) Prior Publication Data
US 2015/0119752 A1    Apr. 30, 2015

Related U.S. Application Data

(60) Provisional application No. 61/896,180, filed on Oct. 28, 2013.

(51) Int. Cl.
*A61B 5/03* (2006.01)
*A61B 5/00* (2006.01)
*A61M 27/00* (2006.01)

(52) U.S. Cl.
CPC ............ *A61B 5/031* (2013.01); *A61B 5/0002* (2013.01); *A61B 5/6852* (2013.01); *A61B 5/6868* (2013.01); *A61M 27/006* (2013.01); *A61M 2205/3344* (2013.01); *A61M 2205/3523* (2013.01); *A61M 2206/11* (2013.01)

(58) Field of Classification Search
CPC ............................................. A61B 3/05–5/038
See application file for complete search history.

(56) References Cited

U.S. PATENT DOCUMENTS

| 4,114,606 A | 9/1978 | Seylar |
| 4,127,110 A | 11/1978 | Bullara |

(Continued)

FOREIGN PATENT DOCUMENTS

| EP | 0018207 B1 | 3/1984 |
| WO | 9732519 A1 | 9/1997 |

(Continued)

OTHER PUBLICATIONS

Seaver, Chad Eric, "An Implantable Low Pressure Biosensor Transponder," Master's Thesis, University of Tennessee, Dec. 2013, http://trace.tennessee.edu/utk_gradthes/2640.

*Primary Examiner* — Adam J Eiseman
(74) *Attorney, Agent, or Firm* — Meunier Carlin & Curfman LLC

(57) ABSTRACT

An implantable subcutaneous device to measure internal body pressure and wirelessly transmit information corresponding to the measured internal body pressure, including a pressure sensor to sense pressure of a particular region of a body of a patient and output a pressure signal corresponding to the sensed pressure, an encoder to receive the pressure signal and encode a signal to produce a sensor information signal to be transmitted to an ex vivo receiver, a transceiver to receive the sensor information signal from the encoder and transmit the sensor information signal to the ex vivo receiver, and a biocompatible housing in which to enclose the pressure sensor, encoder, and transceiver.

33 Claims, 4 Drawing Sheets

(56) References Cited

U.S. PATENT DOCUMENTS

| | | | | |
|---|---|---|---|---|
| 4,281,667 A * | 8/1981 | Cosman | A61B 5/0002 | 600/438 |
| 4,354,506 A * | 10/1982 | Sakaguchi | A61B 5/031 | 600/561 |
| 4,471,786 A | 9/1984 | Inagaki et al. | | |
| 4,593,703 A * | 6/1986 | Cosman | A61B 5/0002 | 600/438 |
| 4,627,443 A * | 12/1986 | Chubbuck | G01L 11/00 | 600/561 |
| 4,653,508 A * | 3/1987 | Cosman | A61B 5/0002 | 600/561 |
| 4,660,568 A * | 4/1987 | Cosman | A61B 5/0002 | 600/561 |
| 4,846,191 A * | 7/1989 | Brockway | A61B 5/0031 | 128/903 |
| 5,048,515 A * | 9/1991 | Sanso | A61M 16/00 | 128/204.18 |
| 5,400,794 A | 3/1995 | Gorman | | |
| 5,440,931 A * | 8/1995 | Wiegand | G01L 9/0073 | 73/718 |
| 5,683,432 A * | 11/1997 | Goedeke | A61N 1/37223 | 607/31 |
| 6,073,050 A * | 6/2000 | Griffith | A61N 1/37223 | 340/870.24 |
| 6,083,174 A * | 7/2000 | Brehmeier-Flick | A61B 5/031 | 600/486 |
| 6,113,553 A | 9/2000 | Chubbuck | | |
| 6,135,718 A * | 10/2000 | Yang | H02P 7/28 | 318/471 |
| 6,248,080 B1 * | 6/2001 | Miesel | A61B 5/0215 | 600/311 |
| 6,533,733 B1 * | 3/2003 | Ericson | A61B 5/0031 | 128/903 |
| 7,015,826 B1 * | 3/2006 | Chan | A01K 11/006 | 340/10.41 |
| 7,290,454 B2 | 11/2007 | Liu | | |
| 7,413,547 B1 | 8/2008 | Lichtscheidl et al. | | |
| 7,464,599 B2 * | 12/2008 | Silverbrook | B60C 23/0408 | 73/708 |
| 8,366,633 B2 | 2/2013 | Wolf | | |
| 2002/0052563 A1 * | 5/2002 | Penn | A61B 5/0215 | 600/561 |
| 2002/0120200 A1 * | 8/2002 | Brockway | A61B 5/0028 | 600/488 |
| 2002/0151770 A1 * | 10/2002 | Noll, III | A61B 5/0031 | 600/300 |
| 2004/0106874 A1 | 6/2004 | Eigler et al. | | |
| 2004/0260229 A1 * | 12/2004 | Meir | A61B 5/031 | 604/9 |
| 2005/0096562 A1 * | 5/2005 | Delalic | A61B 5/0031 | 600/561 |
| 2005/0109935 A1 * | 5/2005 | Manlove | B60R 21/01516 | 250/300 |
| 2006/0020224 A1 * | 1/2006 | Geiger | A61B 5/031 | 600/561 |
| 2006/0116602 A1 * | 6/2006 | Alden | A61B 5/036 | 600/561 |
| 2006/0144155 A1 * | 7/2006 | Liu | A61B 5/02152 | 73/753 |
| 2007/0167867 A1 * | 7/2007 | Wolf | A61B 5/0017 | 600/561 |
| 2008/0139959 A1 * | 6/2008 | Miethke | A61B 5/0031 | 600/561 |
| 2008/0262320 A1 * | 10/2008 | Schaefer | A61B 5/0008 | 600/300 |
| 2009/0036751 A1 * | 2/2009 | Lutze | A61B 5/031 | 600/300 |
| 2009/0069648 A1 * | 3/2009 | Irazoqui | A61B 3/16 | 600/302 |
| 2009/0143696 A1 * | 6/2009 | Najafi | A61B 5/0031 | 600/561 |
| 2009/0204019 A1 * | 8/2009 | Ginggen | A61B 5/031 | 600/561 |
| 2009/0299216 A1 * | 12/2009 | Chen | A61B 3/16 | 600/561 |
| 2011/0160560 A1 | 6/2011 | Stone | | |
| 2011/0224595 A1 * | 9/2011 | Pedersen | A61B 5/031 | 604/8 |
| 2012/0174681 A1 * | 7/2012 | Drewes | G01L 9/0075 | 73/724 |
| 2012/0247218 A1 * | 10/2012 | Crivelli | G01L 9/0073 | 73/724 |
| 2012/0265028 A1 | 10/2012 | Hughes et al. | | |
| 2013/0109990 A1 * | 5/2013 | Akingba | A61B 5/03 | 600/529 |
| 2013/0194540 A1 * | 8/2013 | Pugh | H01Q 1/22 | 351/159.03 |
| 2014/0135647 A1 | 5/2014 | Wolf, II | | |
| 2014/0276180 A1 * | 9/2014 | Dextradeur | A61B 5/0006 | 600/544 |
| 2014/0298884 A1 * | 10/2014 | Mindlin | G01L 9/0047 | 73/1.63 |
| 2015/0005800 A1 * | 1/2015 | Anile | A61M 27/006 | 606/192 |

FOREIGN PATENT DOCUMENTS

| | | |
|---|---|---|
| WO | 2011018706 A1 | 2/2011 |
| WO | 2012112819 A2 | 8/2012 |
| WO | 2014076620 A1 | 5/2014 |

* cited by examiner

IMPLANTABLE BIO-PRESSURE TRANSPONDER

CROSS-REFERENCE TO RELATED APPLICATIONS

This application claims the benefit of U.S. Provisional Patent Application Ser. No. 61/896,180, filed on Oct. 28, 2013, the contents of which are incorporated herein by reference in its entirety.

FIELD OF INVENTION

The present general inventive concept relates to systems and methods of assessing bodily fluid pressures, such as cerebral spinal fluid (CSF), and, more particularly, to a pressure sensor and transponder, and the methods of carrying out the same.

BACKGROUND

The human body is comprised of various organs that generate, or are subject to, a variety of pressures. These pressures are primarily induced externally due to gravity, and include atmospheric compression and body weight opposition. However, there are also a wide range of pressures induced within the body itself. These pressures include, for example, those generated by the cardiovascular system, urinary system, digestive tract, musculoskeletal system, and central nervous system, among others. Most of these pressures are critical for good health and must be precisely regulated. Blood pressure of the cardiovascular system and cerebral spinal fluid of the central nervous system are two such components that need to be precisely maintained. The ability to continuously monitor these pressures would allow for early detection and intervention in the event regulation becomes impaired.

Long term monitoring of intracranial pressures (ICP) induced by cerebral spinal fluid (CSF) is of particular interest since chronic elevated ICP is common in patients with hydrocephalus, and can become life threatening if left untreated. However, current state of the art monitoring devices typically require sensors to be placed within the brain and be tethered to bedside equipment in order to measure and/or monitor the pressure. Such measurements typically only allow ICP monitoring for days at a time, and require a clinical setting to facilitate these complicated and risky measurements. Patient position becomes critical for these systems, and since the sensor must be tethered from within the brain to a bedside instrument, the risk of infection is high.

Intracranial pressure is among the most critical pressures found within the body. Intracranial hypotension can lead to ruptured blood vessels and hematomas, while CSF hypertension can lead to decreased blood perfusion within the brain. Either case can quickly become life threatening and affects one to two percent of the population congenitally by hydrocephalus, or can be acquired, for example, due to brain tumor, traumatic obstruction, or damage to the arachnoid villi from meningitis, and other similar situations. Therefore, there exists a need for a less invasive system and method of measuring/monitoring such critical pressures, and that will not be as limiting to the patient's mobility as the conventional methods, but also be sustainable.

BRIEF SUMMARY

The present general inventive concept, in various example embodiments, includes a self-contained long term implantable bio-pressure sensor and transponder device to facilitate extended in-vivo CSF pressure measurement readouts in a non-invasive manner.

Additional aspects and advantages of the present general inventive concept will be set forth in part in the description which follows, and, in part, will be obvious from the description, or may be learned by practice of the present general inventive concept.

Various aspects and advantages of the present general inventive concept may be achieved by example embodiments such as an implantable subcutaneous device to measure internal body pressure and wirelessly transmit information corresponding to the measured internal body pressure, including a pressure sensor to sense pressure of a particular region of a body of a patient and output a pressure signal corresponding to the sensed pressure, an encoder to receive the pressure signal and encode a signal to produce a sensor information signal to be transmitted to an ex vivo receiver, a transceiver to receive the sensor information signal from the encoder and transmit the sensor information signal to the ex vivo receiver, and a biocompatible housing in which to enclose the pressure sensor, encoder, and transceiver.

The device may further include an inlet pressure port provided to the biocompatible housing through which fluid pressure is transferred to the pressure sensor.

The device may further include a catheter extending from the inlet pressure port to the particular region of the body of the patient through which body fluid may flow to the pressure sensor.

The device may further include a shunt distal catheter configured to receive the body fluid received through the catheter extending to the particular region of the body of the patient to drain the body fluid to a remote collection site.

The device may further include a tee connection configured to connect the shunt distal catheter to the inlet pressure port to receive the body fluid from the catheter extending to the particular region of the body of the patient.

The device may further include a reference pressure port provided to the biocompatible housing through which a reference fluid pressure is transferred to the pressure sensor.

The device may further include a fluid containing body coupled to the reference pressure port such that a pressure on a fluid in the fluid containing body is transferred to the pressure sensor.

The device may further include a structural support provided to the fluid containing body to prevent incidental pressures incident to the fluid containing body.

The fluid containing body may be configured to extend inwardly to an internal location in the patient to provide in vivo calibration of the pressure sensor.

The device may further include an antenna configured to be external to the biocompatible housing and in electrical communication with the transceiver to transmit the sensor information signal.

The device may further include a power supply unit to provide power to the device, and to receive power from the transceiver that is induced from an ex vivo induction unit.

The device may further include a power transceiver, and a power supply unit to receive power from the power transceiver that is induced from an ex vivo induction unit, and to provide power to the device.

The encoder may include a sweep generator unit to output a ramp signal to be compared to the pressure signal.

The encoder may further include a comparator to compare the pressure signal to the ramp signal to generate a stop signal in response to the ramp signal being equal to the pressure signal.

The encoder may further include an oscillator to output the sensor information signal such that an oscillator output is generated until the ramp signal reaches a level of the pressure signal, and is stopped in response to the ramp signal becoming equal to or greater than the pressure signal, during each cycle of the ramp signal so that the oscillator output is proportional in time relative to pressure incident on the pressure sensor.

The encoder may further include a signal delay unit to facilitate a settling time of the pressure sensor to turn on the oscillator and sweep generator.

The pressure sensor may supply the pressure signal in proportion to pressure by means of piezo-resistance, capacitive or inductive reactance, or optical interferometry.

Various aspects and advantages of the present general inventive concept may be achieved by example embodiments such as a system to measure internal body pressure and wirelessly transmit information corresponding to the measured internal body pressure to be displayed at a location external to a patient, the system including an implantable subcutaneous device comprising, a pressure sensor to sense pressure of a particular region of a body of a patient and output a pressure signal corresponding to the sensed pressure, an encoder to receive the pressure signal and encode a signal to produce a sensor information signal to be transmitted to an ex vivo location, an internal transceiver to receive the sensor information signal from the encoder and transmit the sensor information signal to the ex vivo location, and a biocompatible housing in which to enclose the pressure sensor, encoder, and transceiver, an ex vivo transceiver to receive the sensor information signal transmitted from the internal transceiver of the subcutaneous device, a demodulator to decode the sensor information signal received by the ex vivo transceiver, and a display unit to display information corresponding to the pressure sensed by the pressure sensor.

The system may further include a communications means through which the internal transceiver and ex vivo transceiver communicate.

The communications means may include respective antennas provided to the internal and ex vivo transceivers.

The ex vivo transceiver may supply power to the internal transceiver of the subcutaneous device through induction.

The implantable subcutaneous device may further include a power transceiver to receive power through induction from the ex vivo transceiver or other ex vivo device to power the implantable subcutaneous device.

The internal transceiver may be configured as a first antenna, and the power transceiver may be configured as a second antenna.

The encoder may use the received pressure signal to modulate a communications alternating current frequency by means of pulse width modulation to produce the sensor information signal.

Various aspects and advantages of the present general inventive concept may be achieved by example embodiments such as an implantable pressure sensor system for the measurement of fluid pressures within a body, the system including a pressure sensor to produce a pressure signal proportionate to a sensed pressure, encoding circuitry to receive the pressure signal from the pressure sensor and to modulate a communications alternating current frequency to produce a sensor information signal, and a telemetry unit to receive electromagnetic transcutaneous powering and to transmit the sensor information signal, optionally on a single antenna or on separate antennas, to a receiver unit external to the body, wherein the pressure sensor, encoding circuitry, and telemetry unit are configured to be implanted in a subcutaneous manner in the body.

The sensor information signal may be modulated by amplitude, frequency, phase, or temporally to encode information proportional to the pressure signal.

The pressure sensor may be a differential pressure sensor having an input port to measure a desired body pressure, and a reference port may be used to detect a predetermined or predictable offset pressure for measuring desired in-vivo fluid pressure and to calibrate the pressure sensor.

The pressure sensor may include a sealed calibrated pressure signal reference chamber in which the pressure signal is proportional to a pre-determined pressure reference of the reference chamber.

The reference chamber may be substantially a vacuum.

The reference chamber may contain a gas.

The reference chamber may contain a liquid.

Other features and aspects may be apparent from the following detailed description, the drawings, and the claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which.

DETAILED DESCRIPTION

Reference will now be made to the example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

According to various examples of the present general inventive concept, a self-contained long term implantable bio-pressure sensor device to facilitate extended in-vivo CSF pressure measurement readouts in a non-invasive manner is provided. Example embodiments of the present general inventive concept can be utilized to realize a non-invasive, real time, in-vivo pressure measurement transponder such as that which would be used to assess CSF pressures in a hydrocephalus patient.

Figure 1:
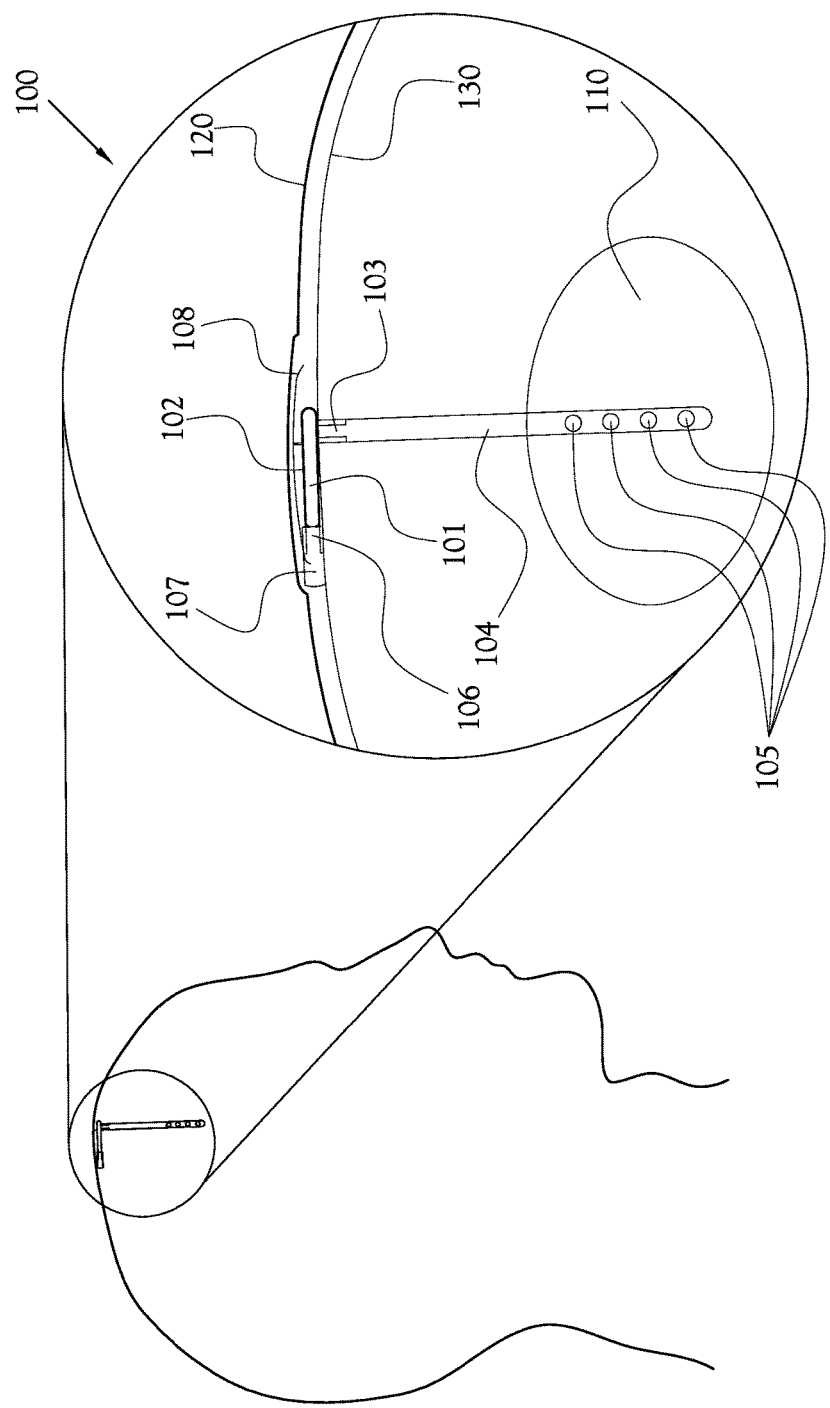
FIG. 1 illustrates an implantable subcutaneous bio-pressure sensor device for ventricular CSF pressure measurement according to an example embodiment of the present general inventive concept.

FIG. 1 illustrates an implantable subcutaneous bio-pressure sensor device for ventricular CSF pressure measurement according to an example embodiment of the present general inventive concept. While the example embodiment illustrated in FIG. 1 shows a subcutaneous sensor device implanted in a region of the head to measure and/or monitor CSF pressure, the present general inventive concept is not limited to such an arrangement or area of the body of the patient. It is understood that various example embodiments of the present general inventive concept may be provided, e.g., implanted, at other regions of the body to monitor other internal body pressures such as, for example, blood pressure of the cardiovascular system. Also, various example embodiments of the present general inventive concept may refer to arrangements including pressure sensors as parts of devices, systems, or simply as pressure sensors.

One advantage of the example embodiment illustrated in FIG. 1 is that the subcutaneous bio-pressure sensor device overcomes the previously described limitations of ICP quantitative measurements in which an external tether is required. Referring to the example embodiment illustrated in FIG. 1, a schematic representation of a subcutaneous bio-pressure sensor device, or transponder, is generally indicated by 100. The bio-pressure sensor 101, which may be commonly referred to as simply the pressure sensor 101 herein, is provided in a subcutaneous position between the scalp 120 and skull 130 of the patient in the example embodiment illustrated in FIG. 1, but may be provided at various other parts of the body in other example embodiments. The bio-pressure sensor can be contained within a biocompatible housing 102 that can be provided with an inlet pressure port 103 through which the fluid in the monitored area of the body arrives via a catheter 104, or, alternatively, a pressure sensitive substance or body contained in the catheter 104, can enable a body induced pressure to be measured by the pressure sensor 101. In other words, in various example embodiments, one or more openings in the catheter 104 may allow relief from the bio-pressure placed on the measured bodily fluid as well as allowing the fluid to be moved toward the pressure sensor 101, and in other various example embodiments the pressure sensitive substance or body may be provided in a body such as the catheter 104 or other containment member which may be flexible such that the bio-pressure may be transferred to the pressure sensitive substance or body, and in turn to the pressure sensor 101. In other example embodiments one or more pressure sensitive components may be provided in the catheter 104 to electrically communicate signals to the pressure sensor 101. In the example embodiment illustrated in FIG. 1, a catheter 104 is coupled to the inlet pressure port 103 and extends into an area 110 of the patient, such as a ventricle of the brain, at which the bio-pressure is desired to be measured/monitored. The catheter 104 of the example embodiment illustrated in FIG. 1 is provided with one or more openings 105 through which the CSF may move into and through the catheter 104 depending on the pressure in the monitored area 110. In various example embodiments of the present general inventive concept, the pressure sensor 101 may additionally, or alternatively, have the option for direct parenchymal sensing as well as other methods described herein or known in the art.

In various example embodiments, a reference pressure port 106 may be provided to the biocompatible housing 102, and may be optionally connected to a catheter or bladder 107 for atmospheric pressure sensing. In various example embodiments the catheter or bladder 107 may be enclosed within a non-collapsible cage or other such rigid structure to remove the effects of erroneous pressure generation due to pressures by forces other than atmospheric pressure such as, for example, ex-vivo contact, patient palpation, movement, tissue growth, etc.

In various example embodiments, the reference pressure port 106 may alternatively be utilized internally for in vivo calibration of the pressure sensor 101 by such means as, for example, a reference tube of reference fluid that contains a known amount of pressure drop, which can be used to occasionally calibrate the pressure sensor 101 against drift, or other errors known to exist within pressure sensors, by occasionally switching between measuring the pressure at the inlet pressure port 103 and the reference pressure port 106 of the pressure sensor 101 to measure the internal reference tube of the pressure port 106 and either utilizing the information for recalibration of the pressure sensor 101 or by warning the healthcare provider if calibration fails.

The device 100 functions as a transponder, so that pressure information detected by the pressure sensor 101 may be communicated to one or more devices or systems outside the patient in a wireless fashion. In various example embodiments, a telemetry antenna 108 may optionally be located external to the biocompatible housing 102, but connected to circuitry of the transponder that will be described in relation to FIG. 2. According to various example embodiments, the telemetry antenna 108 may be of the inductive, optical, or other electromagnetic type of antenna or coupling means for external powering and bidirectional communications.

Figure 2:
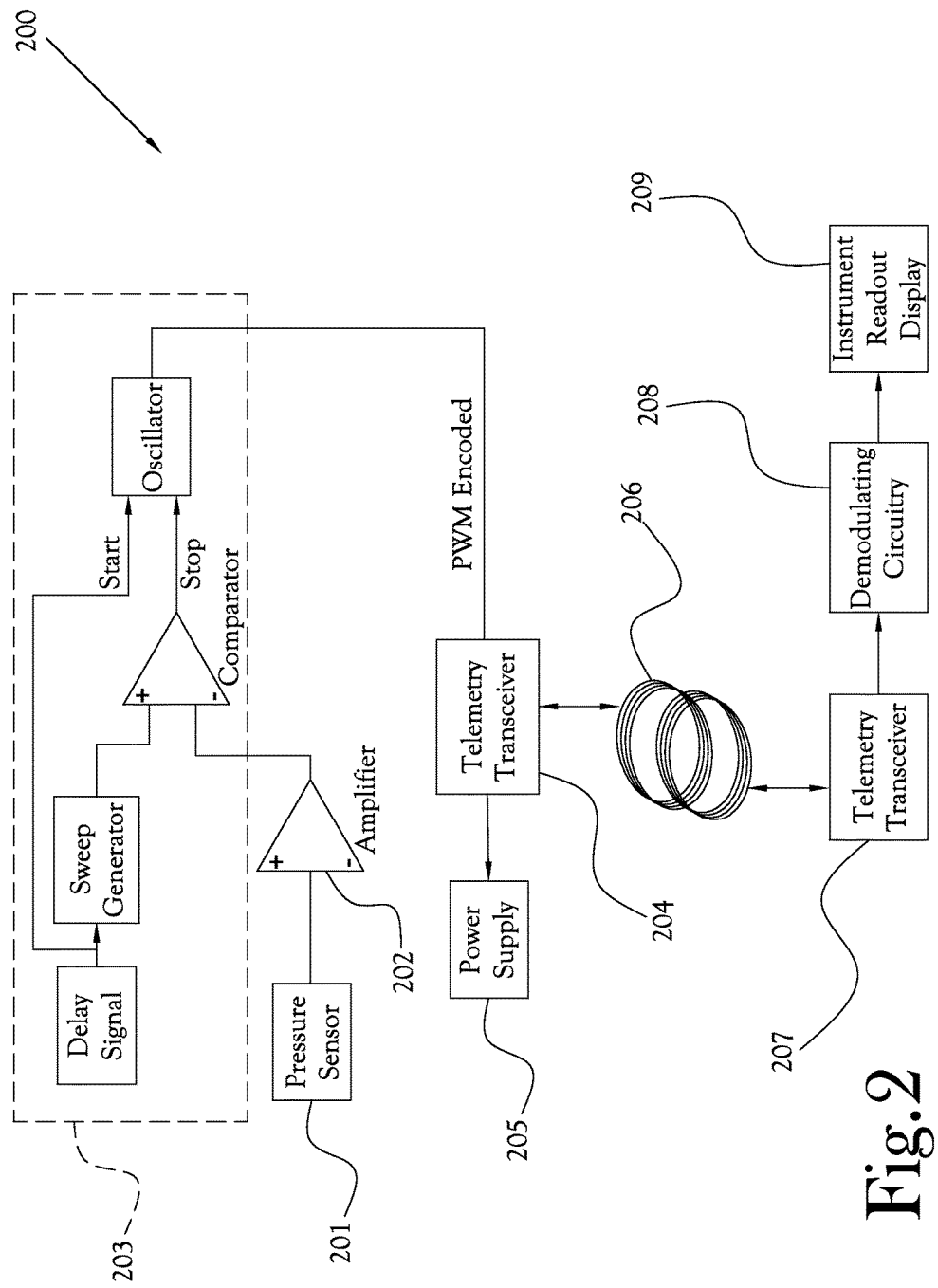
FIG. 2 is a schematic illustration of a bio-pressure sensor system for electronic signal conditioning and transcutaneous non-invasive readout according to an example embodiment of the present general inventive concept.

FIG. 2 is a schematic illustration of a bio-pressure sensor system for electronic signal conditioning and transcutaneous non-invasive readout according to an example embodiment of the present general inventive concept. The example embodiment of the system illustrated in FIG. 2 may be referred to herein simply as the system, or transponder system, 200. The electronic circuitry illustrated in FIG. 2 includes components of a subcutaneous transponder such as the device 100 illustrated in FIG. 1, as well as a transceiver device located ex vivo, or outside and remotely to the patient, to receive information signals from, and in some embodiments provide wireless power to, and/or transmit calibration signals to, the transponder device subcutaneously provided to the patient.

As illustrated in FIG. 2, the pressure sensor 201 supplies a signal proportional to pressure, which may be by means of, for example, piezo-resistive, capacitive or inductive reactance, optical interferometry, or other such devices/methods of a single-ended or differential electrical signal means, which is then conditioned by element 202, which in this example embodiment is an amplifier. An encoder 203 included in the transponder device utilizes the amplified pressure sensor signal output from element 202 to modulate a communications alternating current carrier frequency by means of pulse width modulation. The encoder 203 of this example embodiment includes a signal delay element, a sweep generator, a comparator, and a communications oscillator, as illustrated in FIG. 2. The signal delay element of 203 facilitates a settling time of the pressure sensor 201 at which point the communications oscillator is turned on and the sweep generator then begins to output a ramp signal. The ramp signal is compared by the comparator to the amplified analog pressure sensor signal in order to generate a stop signal to the oscillator once the ramp signal equates to the amplified analog pressure sensor signal provided through the amplifier 202. Thus, the oscillator output is therefore on for the period of time that the ramp signal doesn't equate to the analog pressure sensor signal provided through the amplifier 202, and then is off once the signals equate. In this way, the oscillator output of the encoder 203 is proportional in time relative to the pressure incident upon the pressure sensor 201. A telemetry unit 204, in this example embodiment a transceiver, serves to facilitate power to a power supply unit 205 of the implanted transponder circuit as induced from a transceiver external to the sensor, and also receives the encoder oscillator circuit 203 output signal to correspondingly transmit the output signal across a communications element 206, such as the telemetry antenna(s) 108 of the example device of FIG. 1. In various example embodiments, the communications element may optionally include multiple separate antennas. Almost any communications link can be utilized to facilitate optimal communications of the components in the system including, but not limited to, load shift keying, separate antennas for transmitting and receiving, and the like. Many more examples exist, but characteristics of the communication method such as low power and reliability may be of heightened concern in the course of sound engineering judgment during the design of the various example embodiments.

The communications element 206 may be, for example, of a low frequency inductive link, optical transceiver, or other such electromagnetic coupling, which may include multiple antennas tuned for powering and/or signaling. A telemetry transceiver element 207 of FIG. 2 represents the ex-vivo transceiver which may supply power and also receive and deliver communication signals from and to the bio-pressure transponder device. In this example embodiment of a system, demodulating circuitry 208 can be provided to decode the pressure sensor information signal transmitted from the encoder 203 through the transceiver 204, and received by the telemetry transceiver element 207 before being communicated to an instrument readout display or display unit 209. It is understood that various devices, systems, and methods known in the art may be implemented to provide the demodulation circuitry of the system 200. For example, more or fewer components may be provided to encode the signal to a desired level, an integrated circuit having processing instructions recorded thereon may provide the desired signal processing, and so on. The demodulated signal information is supplied to the readout display unit 209 of the system 200 for human interpretation of the patient's in-vivo pressure. The display unit 209 may be one of any number of display units known in the art. The transceiver 204 of the transponder unit may repetitively output the signal processed by the encoder 203, or may be prompted to begin transmitting the processed signal upon receiving a query from the external receiver 207 of the transponder system 200.

FIG. 2 illustrates the power supply unit 205 receiving power from the telemetry transceiver 204 that is induced through the communications element 206 through the telemetry transceiver element 207. However, in various example embodiments of the present general inventive concept the system 200 may include a separate power transceiver through which power may be inducted from one or more ex vivo devices directly to the power supply unit 205. In various example embodiments, the telemetry transceiver may be configured as a first antenna, and the power transceiver may be configured as a second antenna.

Figure 3:
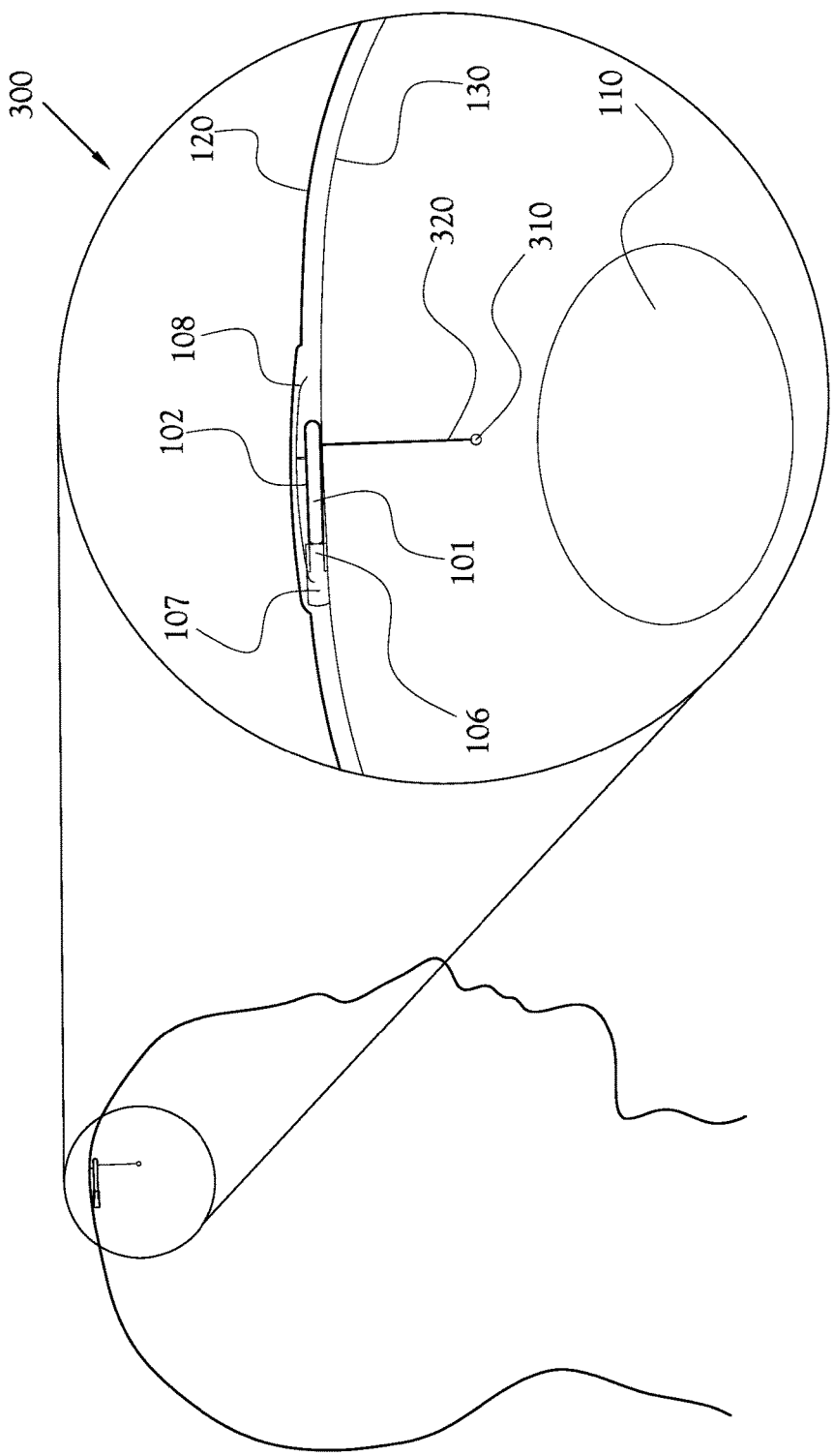
FIG. 3 illustrates an implantable subcutaneous bio-pressure sensor device for parenchymal pressure measurement according to an example embodiment of the present general inventive concept.

As previously discussed, the implantable subcutaneous bio-pressure sensor of the present general inventive concept is not limited to a configuration including a catheter extending into a ventricular area of a patient. For example, a wired or other type sensor may be provided to extend into a tissue of the patient, such as the brain, to measure and/or monitor pressure. FIG. 3 illustrates an implantable subcutaneous bio-pressure sensor device for parenchymal pressure measurement according to an example embodiment of the present general inventive concept. Referring to the example embodiment illustrated in FIG. 3, a schematic representation of a subcutaneous bio-pressure sensor transponder including a parenchymal sensor is generally indicated by 300. According to various example embodiments, the transponder 300 may share many comment elements with the transponder 100 illustrated in FIG. 1. However, in the example embodiment illustrated in FIG. 3, the catheter 104 has been replaced by a parenchymal sensor 310 that extends into a brain tissue area of the patient. In various example embodiments, the parenchymal sensor 310 may be configured to be in electrical communication with the pressure sensor 101 through a wire 320 extending from the pressure sensor 101 to the parenchymal sensor 310, and the wire 320 may be insulated. In various example embodiments, the pressure sensor 101 may be omitted from the transponder 300, and the signal from the parenchymal sensor 310 may be relayed directly to the amplifier 202 or encoder 203 or other such circuitry of the transponder 300 to be temporally encoded for transmission to a device outside the patient.

Figure 4:
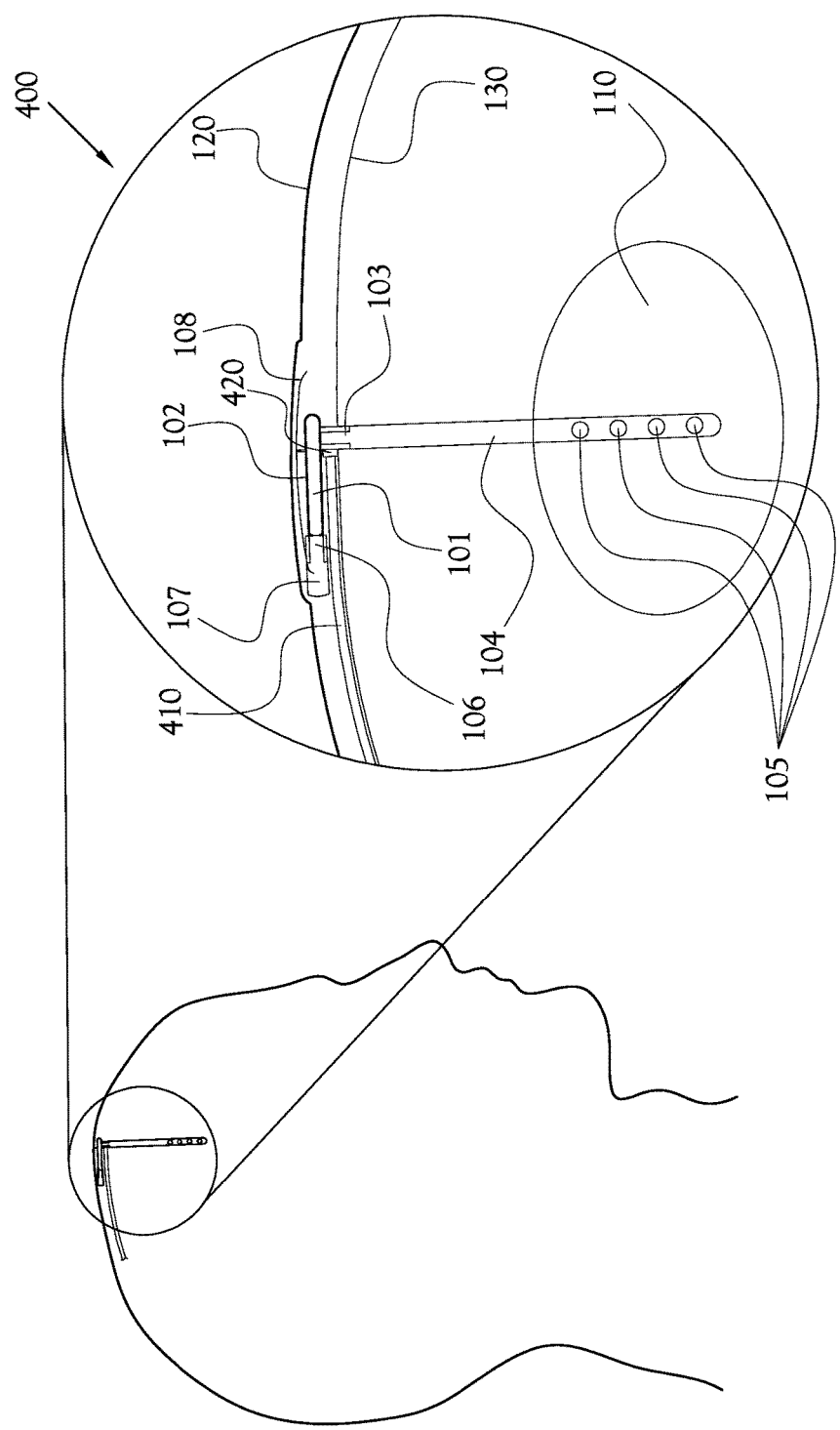
FIG. 4 illustrates an implantable subcutaneous bio-pressure sensor device for ventricular CSF pressure measurement according to another example embodiment of the present general inventive concept.

FIG. 4 illustrates an implantable subcutaneous bio-pressure sensor device for ventricular CSF pressure measurement according to another example embodiment of the present general inventive concept. Referring to the example embodiment illustrated in FIG. 4, a schematic representation of a subcutaneous bio-pressure sensor transponder including a shunt to drain CSF to a remote location in the patient's body is generally indicated by 400. According to various example embodiments, the transponder 400 may share many comment elements with the transponder 100 illustrated in FIG. 1. However, in the example embodiment illustrated in FIG. 4, a shunt distal catheter 410 is configured to be in communication with the transponder 400 to transport CSF collected from the area 110 (such as a ventricle) by the catheter 104 to a remote collection site (not illustrated), such as the peritoneum in the patient's body. In the example embodiment illustrated in FIG. 4, the shunt distal catheter 410 is connected to the inlet pressure port 103 through a tee connector 420 to receive the CSF collected by the catheter 104, and the tee connector 420 provides fluid pressure sensing to the pressure sensor 101. However, in various example embodiments, the shunt distal catheter 410 may be connected to other portions of the transponder 400 and/or catheter 104 to receive the CSF. In various example embodiments, the calibration of the transponder 400 may allow for pressure loss caused by the shunt distal catheter 410, and/or may include CSF pressure in the shunt distal catheter 410.

According to various example embodiments of the present general inventive concept, an implantable pressure sensor system for the measurement of fluid pressures within the human body provides a non-invasive readout method for pressure assessment. Example embodiments of such a system may include a pressure sensor, amplifier, encoding circuitry, and a telemetry unit allowing electromagnetic transcutaneous powering and interrogation of the sensor system.

The pressure sensor may be of the piezo-resistive, capacitive, optical interferometric, or other such type as to ultimately provide an electronic signal proportional to pressure. Such a pressure signal may then be encoded into a sensor information signal whereby the sensor information signal may be modulated by amplitude, frequency, phase, or temporally such as in the case of pulse width modulation (PWM), or any combination thereof, in order to encode information proportional to the measured pressure signal. One such method to encode the pressure sensor signal used in an example embodiment is to compare the electrical pressure sensor output to a predetermined ramp signal, whereby a start to finish signal marker can provide a temporally encoded signal that is essentially a pulse width modulated signal. Such a pulse width modulated signal may modulate an alternating current signal and then be encoded into a carrier frequency suitable for transcutaneous electromagnetic transmission, for example at an optimal carrier frequency greater than one-megahertz. Alternatively, a particular frequency response may be utilized as a signature proportional to the sensed pressure whereby an element of the sensor may be combined with an oscillator to facilitate a shift in resonance or damping to encode the pressure information into a carrier signal. In the case of a damping modulation, temporal encoding can be provided and a receiving circuit can measure the exponential or otherwise decay as representative of a proportional pressure.

Time (i.e., temporal) encoding the pressure signal can lower the power requirement for the transponder, and can markedly improve the signal to noise ratio of the transmission, compared to other types of encoding, such as amplitude modulation. With limited to no processing required to encode the pressure signal, the overall packaging of the transponder can also be much smaller, compared to other types of devices, such as Bluetooth-type devices.

According to various example embodiments, precise pressure measurement may be provided with a differential pressure sensor, whereby a subcutaneous reference port may be utilized to allow a predetermined or predictable offset for the desired in-vivo fluid measurements in order to provide a calibrated adjustment sensor profile. Alternatively, an absolute pressure sensor may be employed with a sealed calibrated pressure signal reference chamber in which signal output from the pressure sensor is proportional to a predetermined pressure reference, which may optionally be a vacuum.

According to various example embodiments, the powering of the long term implantable bio-pressure sensor and transponder device may be provided by means of telemetry whereby an inductive or optical link can transfer signals of such magnitude as to power or charge the implanted electronic circuitry. In a similar means, an inductive, optical, or other electromagnetic method may be utilized by the sensor and transponder device to send signals proportional to the measured in-vivo pressures to a receiver device external to the patient for non-invasive transcutaneous readout by a user.

It is noted that the simplified diagrams and drawings do not illustrate all the various connections and assemblies of the various components, however, those skilled in the art will understand how to implement such connections and assemblies, based on the illustrated components, figures, and descriptions provided herein, using sound engineering judgment.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

It is noted that the simplified diagrams and drawings included in the present application do not illustrate all the various connections and assemblies of the various components, however, those skilled in the art will understand how to implement such connections and assemblies, based on the illustrated components, figures, and descriptions provided herein. Numerous variations, modification, and additional embodiments are possible, and, accordingly, all such variations, modifications, and embodiments are to be regarded as being within the spirit and scope of the present general inventive concept.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

The invention claimed is:

1. An implantable subcutaneous device to measure internal body pressure and wirelessly transmit information corresponding to the measured internal body pressure, comprising:
a pressure sensor configured to sense an inlet pressure of a particular region of a body of a patient via an inlet pressure port, and to sense a reference pressure of a reference chamber via a reference pressure port, wherein the pressure sensor is configured to selectively sense the inlet pressure and the reference pressure so as to compare the reference pressure to the inlet pressure to generate a calibrated inlet pressure signal;

an encoder configured to receive the calibrated inlet pressure signal and encode the calibrated inlet pressure signal to produce a sensor information signal;

a transceiver configured to receive the sensor information signal from the encoder and transmit the sensor information signal to an ex vivo receiver; and a biocompatible housing configured to enclose the pressure sensor, encoder, and transceiver, wherein:

the encoder includes a sweep generator unit, an oscillator, and a signal delay unit, the sweep generator unit outputs a ramp signal to be compared to the calibrated inlet pressure signal, and the signal delay unit is connected to the sweep generator and the oscillator to delay starting of the oscillator and the sweep generator for a sufficient amount of time to facilitate settling of the pressure sensor.

2. The device of claim 1, further comprising a catheter extending from the inlet pressure port to the particular region of the body of the patient through which body fluid may flow to the pressure sensor.

3. The device of claim 2, further comprising a shunt distal catheter configured to receive the body fluid received through the catheter extending to the particular region of the body of the patient to drain the body fluid to a remote collection site.

4. The device of claim 3, further comprising a T-connection configured to connect the shunt distal catheter to the inlet pressure port to receive the body fluid from the catheter extending to the particular region of the body of the patient.

5. The device of claim 1, wherein the reference chamber comprises a fluid containing body coupled to the reference pressure port such that a pressure on a fluid in the fluid containing body is transferred to the pressure sensor.

6. The device of claim 5, further comprising a structural support provided to the fluid containing body to prevent incidental pressures incident to the fluid containing body.

7. The device of claim 5, wherein the fluid containing body is configured to extend inwardly to an internal location in the patient to provide in vivo calibration of the pressure sensor.

8. The device of claim 1, further comprising an antenna configured to be external to the biocompatible housing and in electrical communication with the transceiver to transmit the sensor information signal.

9. The device of claim 1, further comprising a power supply unit to provide power to the device, and to receive power from the transceiver that is induced from an ex vivo induction unit.

10. The device of claim 1, further comprising:
a power transceiver; and
a power supply unit to receive power from the power transceiver that is induced from an ex vivo induction unit, and to provide power to the device.

11. The device of claim 1, wherein the encoder further includes a comparator to compare the calibrated inlet pressure signal to the ramp signal to generate a stop signal in response to the ramp signal being equal to the calibrated inlet pressure signal.

12. The device of claim 1, wherein the oscillator outputs the sensor information signal such that an oscillator output is generated until the ramp signal reaches a level of the calibrated inlet pressure signal, and is stopped in response to the ramp signal becoming equal to or greater than the calibrated inlet pressure signal, during each cycle of the ramp signal so that the oscillator output is proportional in time relative to pressure incident on the pressure sensor.

13. The device of claim 1, wherein the pressure sensor supplies the calibrated inlet pressure signal in proportion to the reference pressure by means of piezo-resistance, capacitive or inductive reactance, or optical interferometry.

14. The device of claim 1, wherein the ex vivo receiver is configured to transmit the reference pressure to pressure sensor.

15. The device of claim 1, wherein the calibrated inlet pressure signal is based on a proportion of the inlet pressure to the reference pressure.

16. The device of claim 15, wherein the reference chamber is sealed and external from the inlet port.

17. The device of claim 1, wherein the pressure sensor selectively senses the reference pressure at predetermined times.

18. The device of claim 1, wherein the encoder is configured to temporally encode the calibrated inlet pressure signal using pulse width modulation (PWM) to produce a temporally encoded sensor information signal.

19. The device of claim 18, wherein the temporally encoded sensor information signal modulates an alternating current signal to encode inlet pressure information into a carrier frequency selected to enhance transcutaneous electromagnetic transmission.

20. A system to measure internal body pressure and wirelessly transmit information corresponding to the measured internal body pressure to be displayed at a location external to a patient, the system comprising:
an implantable subcutaneous device comprising:
a pressure sensor configured to sense an inlet pressure of a particular region of a body of a patient via an inlet pressure port, and to sense a reference pressure of a reference chamber via a reference pressure port, wherein the pressure sensor is configured to selectively sense the inlet pressure and the reference pressure so as to compare the reference pressure to the inlet pressure to generate a calibrated inlet pressure signal,
an encoder configured to receive the calibrated inlet pressure signal and encode the calibrated inlet pressure signal to produce a sensor information signal, the encoder further comprising a sweep generator unit, an oscillator, and a signal delay unit, the sweep generator unit outputs a ramp signal to be compared to the calibrated inlet pressure signal, and the signal delay unit is connected to the sweep generator and the oscillator to delay starting of the oscillator and the sweep generator for a sufficient amount of time to facilitate settling of the pressure sensor,
an internal transceiver configured to receive the sensor information signal from the encoder and transmit the sensor information signal to an ex vivo location, and
a biocompatible housing configured to enclose the pressure sensor, encoder, and transceiver;
an ex vivo transceiver to receive the sensor information signal transmitted from the internal transceiver of the subcutaneous device;
a demodulator to decode the sensor information signal received by the ex vivo transceiver; and
a display unit to display information corresponding to the pressure sensed by the pressure sensor.

21. The system of claim 20, further comprising a communications means through which the internal transceiver and ex vivo transceiver communicate.

22. The system of claim 21, wherein the communications means includes respective antennas provided to the internal and ex vivo transceivers.

23. The system of claim 20, wherein the ex vivo transceiver supplies power to the internal transceiver of the subcutaneous device through induction.

24. The system of claim 20, wherein the implantable subcutaneous device further comprises a power transceiver to receive power through induction from the ex vivo transceiver or other ex vivo device to power the implantable subcutaneous device.

25. The system of claim 24, wherein the internal transceiver is configured as a first antenna, and the power transceiver is configured as a second antenna.

26. The system of claim 20, wherein the encoder uses the received calibrated inlet pressure signal to modulate a communications alternating current frequency by means of pulse width modulation to produce the sensor information signal.

27. An implantable pressure sensor system for the measurement of fluid pressures within a body, the system comprising:
- a pressure sensor configured to produce a calibrated inlet pressure signal proportionate to a sensed inlet pressure, the pressure sensor being configured to sense the inlet pressure via an inlet pressure port, and to sense a reference pressure of a reference chamber via a reference pressure port, wherein the pressure sensor is configured to selectively sense the inlet pressure and the reference pressure so as to compare the reference pressure to the inlet pressure to generate the calibrated inlet pressure signal;
- encoding circuitry configured to receive the calibrated inlet pressure signal from the pressure sensor and to modulate a communications alternating current frequency to produce a sensor information signal;
- a sweep generator unit, an oscillator, and a signal delay unit, the sweep generator unit outputs a ramp signal to be compared to the calibrated inlet pressure signal, and the signal delay unit is connected to the sweep generator and the oscillator to delay starting of the oscillator and the sweep generator for a sufficient amount of time to facilitate settling of the pressure sensor; and
- a telemetry unit configured to receive electromagnetic transcutaneous powering and to transmit the sensor information signal to a receiver unit external to the body;
- wherein the pressure sensor, encoding circuitry, sweep generator unit, oscillator, signal delay unit, and telemetry unit are configured to be implanted in a subcutaneous manner in the body.

28. The system of claim 27, wherein the sensor information signal is modulated by amplitude, frequency, phase, or temporally to encode information proportional to the calibrated inlet pressure signal.

29. The system of claim 27, wherein the pressure sensor is a differential pressure sensor configured to measure a desired body pressure, and the reference pressure port is used to detect a predetermined or predictable offset pressure for measuring desired in-vivo fluid pressure and to calibrate the pressure sensor.

30. The system of claim 27, wherein the pressure sensor includes a sealed calibrated pressure signal reference chamber in which the calibrated inlet pressure signal is proportional to a pre-determined pressure reference of the reference chamber.

31. The system of claim 30, wherein the reference chamber is substantially a vacuum.

32. The system of claim 30, wherein the reference chamber contains a gas.

33. The system of claim 30, where the reference chamber contains a liquid.

* * * * *